United States Patent [19]

Lee

[11] Patent Number: 5,234,459
[45] Date of Patent: Aug. 10, 1993

[54] METHOD OF CONTROLLING THE FLOW OF BLOOD THROUGH A LIMB

[76] Inventor: Hans Lee, Suite 200, 415 Morris St., Charleston, W. Va. 25301

[21] Appl. No.: 912,680

[22] Filed: Jul. 14, 1992

Related U.S. Application Data

[63] Continuation of Ser. No. 438,286, Nov. 20, 1989, abandoned.

[51] Int. Cl.⁵ .............................................. A61B 17/12
[52] U.S. Cl. ..................................... 606/203; 606/202
[58] Field of Search ................ 606/202, 203; 128/677, 128/686, 899

[56] References Cited

U.S. PATENT DOCUMENTS

| | | |
|---|---|---|
| 1,338,578 | 4/1920 | Maeda . |
| 1,473,041 | 11/1923 | Henderson . |
| 1,566,235 | 12/1925 | Sheehan . |
| 1,887,022 | 11/1932 | Hoffmann et al. . |
| 2,068,173 | 1/1937 | Galves . |
| 2,113,534 | 4/1938 | Brown . |
| 2,387,428 | 10/1945 | Brothers . |
| 2,511,269 | 6/1950 | Jones ................................ 606/202 |
| 2,754,825 | 7/1956 | Richmond . |
| 2,893,394 | 7/1959 | Thomsen . |
| 3,050,064 | 8/1962 | Moore et al. . |
| 3,190,444 | 6/1965 | Kelson . |
| 3,279,459 | 10/1966 | Schenker . |
| 3,628,536 | 12/1971 | Glesne . |
| 3,670,735 | 6/1972 | Hazlewood ........................ 606/202 |
| 3,713,446 | 1/1973 | Sarnoff . |
| 3,756,239 | 9/1973 | Smythe . |
| 3,910,280 | 10/1975 | Talonn . |
| 4,125,115 | 11/1978 | Mayo et al. . |
| 4,149,540 | 4/1979 | Hasslinger . |
| 4,182,338 | 1/1980 | Stanulis . |
| 4,273,130 | 6/1981 | Simpson . |
| 4,353,374 | 10/1982 | Rebbe et al. . |
| 4,354,503 | 10/1982 | Golden . |
| 4,566,436 | 1/1986 | Loefqvist . |
| 4,635,635 | 1/1987 | Robinette-Lehman . |
| 4,637,394 | 1/1987 | Racz et al. . |
| 4,760,846 | 8/1988 | Mers Kelly et al. . |
| 4,770,175 | 9/1988 | McEwen . |
| 4,773,419 | 9/1988 | Tountas . |
| 4,781,189 | 11/1988 | Vijil-Rosales . |
| 4,800,900 | 1/1989 | French ................................ 606/202 |

Primary Examiner—C. Fred Rosenbaum
Assistant Examiner—William Lewis
Attorney, Agent, or Firm—Lowe, Price, LeBlanc & Becker

[57] ABSTRACT

A distal forearm tourniquet and method of use therefor for providing a bloodless field during hand surgery is disclosed. The tourniquet includes an adjustable strap or cuff formed with an inflatable balloon on a portion thereof. In use, the tourniquet is placed with the balloon on the dorsal aspect of the forearm between the middle and distal ⅓ and securely tightened to restrict blood flow. In fixed position, the inflatable balloon is located against the dorsal aspect of the forearm and inflated to a desired pressure. The resulting application of the pressure exerted on the dorsal aspect by the balloon and indirect pressure on the volar aspect of the forearm restricts blood flow through the radial and ulnar arteries and the anterior and posterior interosseous arteries. Since the interosseous arteries are nearly hidden between the radius and ulna bones, arterial blood flow therethrough normally cannot be shut off effectively by the application of a conventional pneumatic tourniquet with safe pressure applied around the distal forearm as this exerts circumferential and not bidirectional pressure. The balloon may be provided with an inlet tube containing a one-way check valve preventing expulsion of air from the inflated balloon. A manual sphygmomanometer or compressed air may be used to constantly monitor and regulate inflation pressure.

4 Claims, 2 Drawing Sheets

METHOD OF CONTROLLING THE FLOW OF BLOOD THROUGH A LIMB

This application is a continuation of application Ser. No. 07/438,286, filed Nov. 20, 1989, now abandoned.

TECHNICAL FIELD

The present invention relates generally to apparatus for controlling hemorrhage from, or circulation in, a limb or part of the body, where pressure can be brought on the blood vessels by means of straps, cords, rubber tubes, pads and the like. More particularly, the present invention relates to the use of distal forearm tourniquets for restricting arterial blood flow to provide a bloodless field during hand surgery.

BACKGROUND ART

Tourniquets are commonly used in modern hand surgery to provide a bloodless field. Conventionally, a pneumatic tourniquet cuff is applied around the upper arm and tightened to restrict the blood flow to the hand being surgically treated.

A number of drawbacks occur by use of the aforesaid pneumatic tourniquet cuff applied around the upper arm. For example, when the tourniquet is applied around the upper arm under regional block anesthesia (e.g., axillary, supraclavicular or Brier IV block), patients frequency experience pain under the tourniquet especially if the anesthesia is incomplete. Furthermore, since the tourniquet should be applied high on the upper arm to avoid injury to the radial nerve, pain is also experienced by the ischemia and the pressure against unanesthetized tissue high in the upper arm. As the pain increases, the only remedy other than deep sedation or general anesthesia is to release the tourniquet which floods the surgical field with blood causing difficulty in completing the surgery. Another disadvantage of the upper arm tourniquet is the possibility of distal migration or movement on the arm. Although a rare occurrence, if unnoticed (since the upper arm tourniquet is completely covered with surgical sheets and drapes), such migration of the upper arm tourniquet can cause nerve damage, especially to the radial nerve.

Preservation of active movement of fingers is crucial in certain procedures, such as tenolysis, to observe the adequacy of the surgery. Such preservation of active movement is not easily obtainable with an upper arm tourniquet and major regional block or general anesthesia since the muscles are paralyzed from the anesthesia. Furthermore, in many cases, the major regional block anesthesia of the types mentioned above are to allow the use of the upper arm tourniquet since the tourniquet causes significant pain without anesthesia. Although rare, complications resulting from these major regional block anesthesia can be detrimental.

Another problem associated with the conventional pneumatic tourniquet cuff applied around the forearm is the inability of such a cuff to adequately restrict blood flow through all four major arteries within the forearm. It is particularly difficult to restrict blood flow through the anterior and posterior interosseous arteries which are hidden in a "valley" between the radial and ulna bones.

SUMMARY OF THE INVENTION

It is accordingly one object of the present invention to provide a new type of tourniquet that may be applied to the distal forearm to establish a bloodless field during hand surgery by application of direct pressure against a particular portion of the distal forearm to regulate blood flow through the major arteries within the forearm.

Another object of the invention is to provide a distal forearm tourniquet equipped with an inflatable balloon positionable against the forearm between the middle and distal ⅓ of the dorsal aspect to control arterial blood flow.

Another object is to provide a distal forearm tourniquet that may be used without major regional block anesthesia for relatively short surgical procedures.

Still a further object is to provide a tourniquet that may be used on other parts of the body and which is provided with an inflatable balloon for creating a direct pressure acting directly against a part of the body lying adjacent the balloon and indirectly against the opposite side of the same part of the body.

A tourniquet, in accordance with the present invention, comprises a strap with fastening material at end portions thereof for securing opposite ends of the strap together in an operative position encircling a limb or a part of a patient's body to restrict blood flow. An inflatable balloon, mounted on rigid hard backing material attached to the strap, or mounted to a rigid portion of the strap, is adapted to press against the limb or part upon inflation and thereby apply the pressure directly against a portion of the limb or part lying adjacent the balloon and indirectly against the opposite portion of the limb or part lying adjacent the strap, i.e., creating a sandwiching pressure.

The balloon preferably includes an inlet valve through which pressurized air is admitted into the balloon to inflate same using a pressurized external air source. The inlet valve preferably includes an inlet tube having tubular side walls with a one-way check valve in the tube for preventing unintentional deflation of the balloon. The one-way valve is operable to open, upon manually pinching the tubular side walls together, to permit deflation of the balloon.

More particularly, the strap preferably includes a rigid base (or hard backing of balloon) and the balloon is a flexible member having peripheral edges sealed to the base to define an inflatable chamber therebetween. The strap further includes a flexible portion adapted to encircle the patient's limb or part and which is secured to the base. A first portion of the flexible strap has one of hook or loop members thereon and the second portion of the strap has the other of hook and loop members. When attached to encircle the patient's limb or body part, the hook and loop members on the first and second portions of the strap engage each other to adjustably and tightly fasten the tourniquet strap to the limb or part. When applying the strap to the limb or part, the rigid base containing the inflatable balloon is positioned against a desired area of the limb or part which is the dorsal aspect of the forearm.

The rigid base is preferably inflexible plastic or other material not bendable or flexible in a direction perpendicular to its plane. The balloon is preferably a resilient stretchable material whose peripheral edges are heat-sealed to the plastic base. The inlet tube projects outward from the balloon beyond the base for easy connection to the external pressurized air source.

In accordance with another feature of the invention, the objects of the present invention may optionally be achieved by the use of a tourniquet strap provided with a separate inflatable means adapted to be positioned against a desired area of the patient's limb or part at the time the tourniquet strap is applied thereto. The separate inflatable means may then be inflated to exert a radial pressure against the desired area.

A method of controlling the flow of blood through a limb or part of a patient's body is also disclosed. The method, in accordance with the present invention, comprises the steps of wrapping and tightening a tourniquet about the limb or part to apply a generally uniform tightening pressure around the encircled limb. An inflatable member located between the strap and a desired area of the limb or part is then inflated to exert a radial pressure directly against the desired area.

Preferably, the tourniquet is applied as a distal forearm tourniquet for use during hand surgery. The tourniquet is applied to the forearm between the middle and distal ⅓ with the inflatable member pressing against the dorsal aspect and the strap against the palm side of the forearm to apply direct pressure against all four arteries.

The inflatable member is preferably a balloon formed along the rigid portion of the strap which is positioned so as to directly contact the area to which direct pressure is to be applied. The balloon may include an inlet valve containing a one-way check valve to allow for inflation of the balloon to a predetermined pressure without releasing the pressurized air within the balloon after inflation occurs. The check valve may be of a type to deflate the contents of the balloon upon pinching the tubular side walls of the inlet valve together.

The method of the present invention also contemplates inflation, monitoring and adjustment of the inflation pressure within the balloon throughout the surgical procedure to constantly maintain a desired inflation pressure during use. A manual sphygmomanometer may be used to both inflate the balloon and monitor the pressure therewithin.

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BEST MODE FOR CARRYING OUT THE INVENTION

Figure 1:
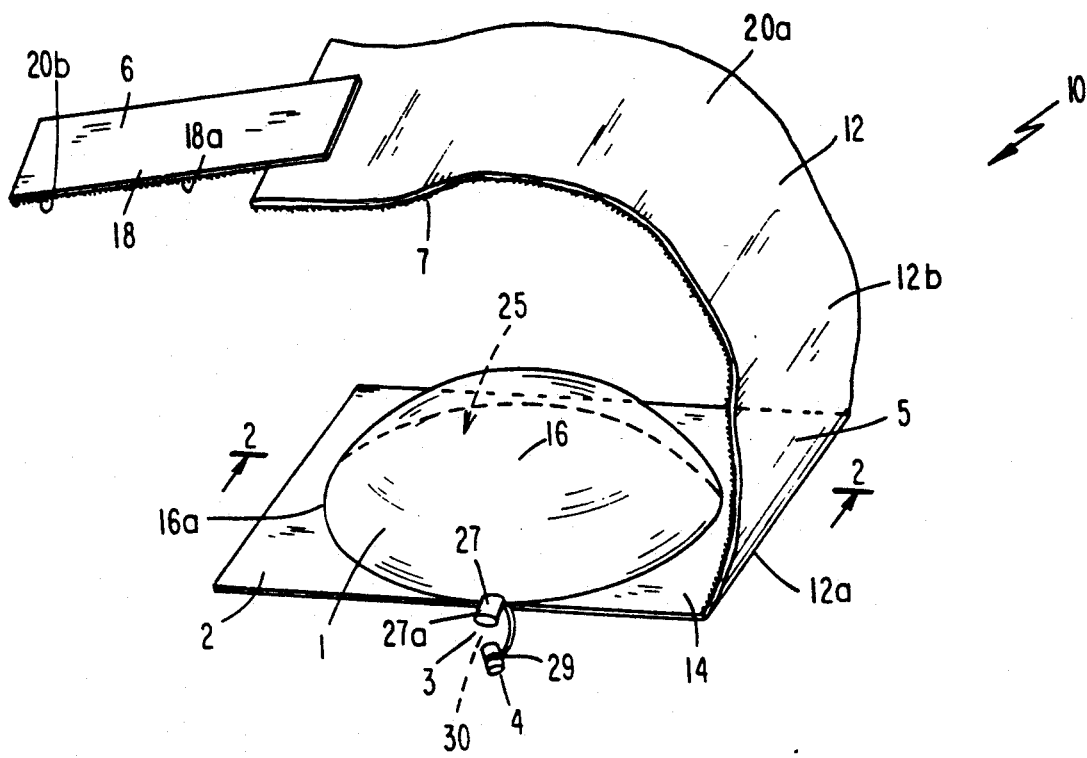
FIG. 1 is a perspective view of a distal forearm tourniquet constructed in accordance with the present invention.
Figure 2:
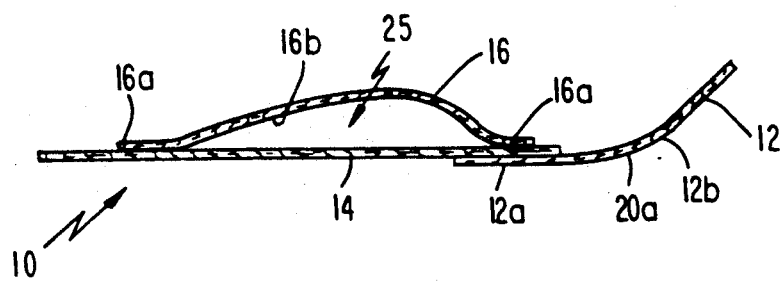
FIG. 2 is a sectional view taken along the line 2—2 of FIG. 1.
Figure 3:
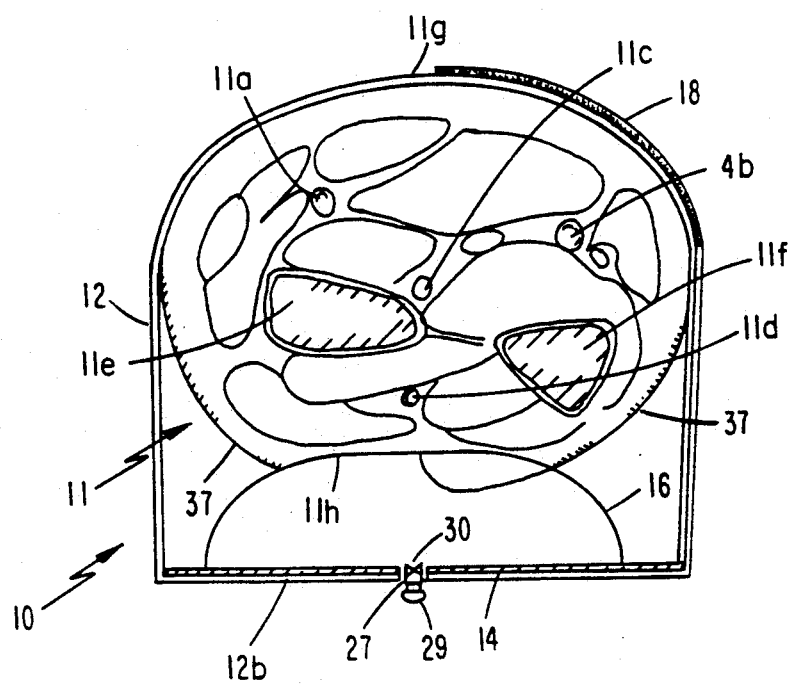
FIG. 3 is a sectional view depicting the tourniquet of the invention applied to the distal forearm of a patient.

FIG. 1 is an illustration of a distal forearm tourniquet 10 constructed in accordance with the present invention for preferred use applied to the dorsal aspect of a patient's forearm 11 between the middle and distal ⅓ to provide a bloodless surgical field during hand surgery by restricting circulation through the radial artery 11a, ulnar artery 1b and the anterior and posterior interosseous arteries 11c, 11d. Since the anterior and posterior interosseous arteries 11c, 11d are hidden in a "valley" formed between the radial and ulna bones 11e and 11f as depicted in FIG. 3, the application of a uniform tightening pressure such as achieved by a conventional tourniquet cuff is insufficient to exert a proper constricting force to prevent blood flow through these two arteries. The present invention is advantageously provided with an inflatable means in the form of a inflatable balloon or bulb formed on one portion of the tourniquet strap. During use, as depicted in FIG. 3, inflation of the bulb or balloon exerts a bidirectional force acting directly against the backside 11h and indirectly through the strap against the underside or palm side 11g of the forearm 11 and this combined application of force is exerted directly against the radial, ulnar, anterior and posterior interosseous arteries 11a, 11b, 11c, 11d to restrict blood flow and provide for a bloodless surgical field.

Forearm tourniquet 10 in accordance with the present invention comprises a flexible strap 12 having one end portion 12a thereof attached to a rigid base 14 to which is mounted a balloon 16. The opposite end of flexible strap 12 carries a second flexible strap portion 18. One surface 12b of the strap 12 facing away from balloon 16 is provided with one of hook or loop members 20a (e.g., male or female VELCRO TM material) while one surface 18a of the second strap 18 facing in the same direction of the strap as balloon 16 is provided with the other of hook or loop members 20b. In operative position of tourniquet 10 applied to the forearm 11 or other part of the body, the second or distal strap portion 18 is engageable with the fastening material 20a on the first strap portion 12 to securely and tightly fasten tourniquet 10 to the patient's limb or other body part.

The mounting base 14, as mentioned above, is preferably a rigid rectangular piece of material, such as plastic, to which peripheral edges 16a of balloon 16 are preferably heat-sealed to define an inflatable chamber 25 between an inward facing surface 16b of balloon 16 and the base 14. The balloon 16 further includes an inlet opening to which is attached an inlet tube 27 provided with a plug or cap 29 for sealing the inflation chamber 25 upon inflation of same to a predetermined desired pressure. Optionally, the inlet tube 27 may also be provided with a conventional one-way valve 30 which prevents balloon deflation until such time as the side walls 27a of tube 27 are pinched together to open the one-way valve 30.

Figures 4, 5:
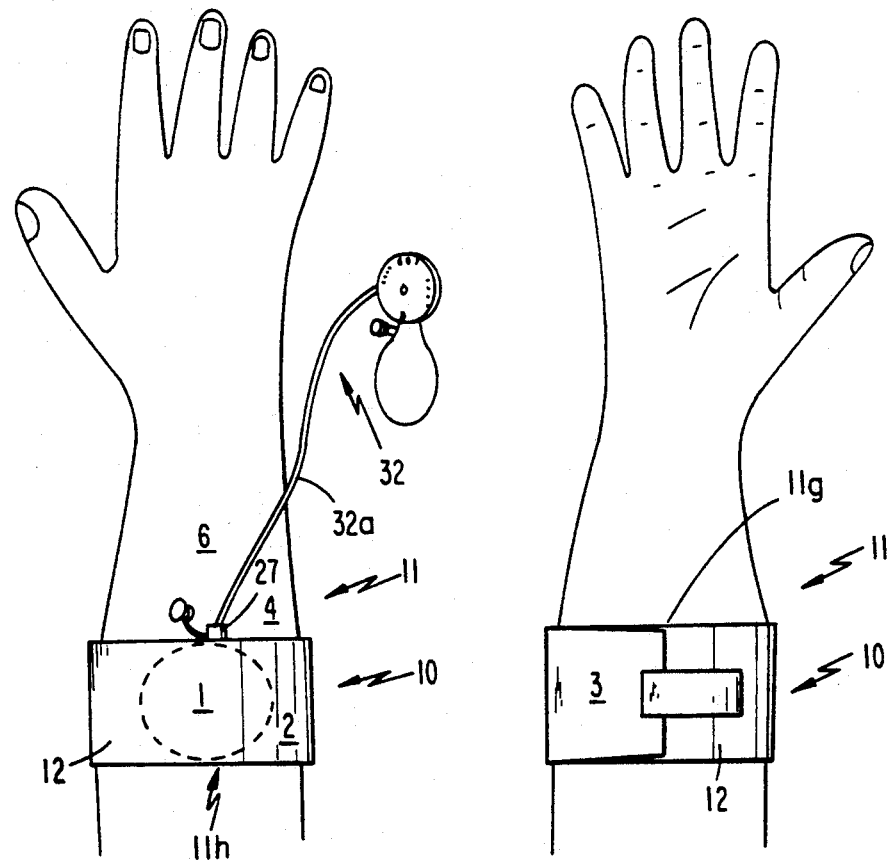
FIGS. 4 and 5 depict, in schematic view, opposite sides of the forearm with the tourniquet applied to the mid-distal ⅓.

With reference to FIG. 3, a preferred use of tourniquet 10 in accordance with a novel method of the present invention is the application of the tourniquet with the balloon part against the dorsal aspect of the forearm 11 between the middle and distal ⅓ such as also depicted in FIGS. 4 and 5, with the balloon 16 engaging the dorsal aspect side 11h of the forearm. The strap portions 12 and 18 in conjunction with the base 14 completely encircle the forearm 11, preferably more than once for security, and the strap is then tightened in a conventional manner by engagement of the hook and loop fasteners 18a, 20a. Thereupon, an external source of pressurized air via a manual sphygmomanometer 32 or from a conventional compressed gas tank (not shown) is connected to the inlet tube 27 to inflate the balloon 16 so that it creates the desired pressure against both sides 11g,11h of the forearm 11. Thereby, the pressure provided by straps 12,18 against the volar aspect 11g in combination with the pressure exerted by balloon 16 against the dorsal aspect 11h of the distal forearm 11, advantageously serves to restrict blood flow through the two interosseous arteries as well as the radial and ulnar arteries which comprise the main four arteries within the forearm.

FIG. 3 also depicts an alternative embodiment to the forearm tourniquet 10 depicted in FIG. 1. The tourniquet of FIG. 3 is substantially identical to the tourniquet 10 of FIG. 1 except that the inlet tube 27 is formed in the base 14, not in the balloon side wall and therefore projects downwardly below a bottom surface of the base for connection to a manual sphygmomanometer 32 or a conventional compressed gas tank (through an air feeding tube such as IV tubing, not shown). When wrapping the strap 12 around the rigid base, the excess strapping portion 12b outwardly adjacent the base must not cover the inlet tube 27.

Although balloon 16 can be pressurized in the manner described above and then capped with plug 29 until such time as removal of the tourniquet is desired by deflation of balloon 16 and removal of straps 12,18, it will be appreciated that the tubing 32a from the manual sphygmomanometer 32 or air feeding tube from the compressed gas tank may remain connected to inlet tube 27 during use of the tourniquet to simultaneously monitor and maintain a constant desired pressure within chamber 25.

Once the strapping is wrapped tightly around the patient's forearm 11 and secured via fasteners 18a,20a, the patient's hand is then typically closed tightly and the fist and forearm distal to the tourniquet is wrapped tightly with elastic bandage to exanguinate the hand and forearm. The air feeding tube 32a is then connected to the inlet tube 27 and the balloon 16 is inflated typically to a pressure of about 250 mm/Hg or to two times the systolic pressure. The air feeding tube 32a is then disconnected and the plug 29 is inserted into its open end to seal the inflation chamber 25. In the alternative, as mentioned above, the tubing 32a may remain in the inlet tube so as to continuously monitor and adjust the inflation pressure of the tourniquet. Thereupon, the plug 29 is removed from the entrance opening of inlet tube 27 (or the air feeding tube is disconnected), the side walls of the inlet tube 27 are pinched to open the one-way check valve 30 to deflate the balloon 16 to then enable removal of the tourniquet strapping in the manner described above.

As mentioned above, if a conventional pneumatic tourniquet cuff is applied around the distal forearm, arterial blood flow is not effectively restricted with acceptable pressure since the anterior and posterior interosseous arteries 11c,11d are hidden in the "valley" between the radius and ulna bones 11e,11f. With the distal forearm tourniquet 10 of the present invention, pressure is exerted bidirectionally, i.e., the pressure against the volar aspect of the forearm provided by the tourniquet strapping 12 and the balloon inflation pressure acting directly on dorsal aspect of the forearm effectively shut off blood flow of the four arteries within the arm with the acceptable predetermined pressures set forth above. Further, regardless of the type of regional anesthesia used (e.g., blocks or local), the pain related to the distal forearm tourniquet 10 of the invention is considerably less than the pain caused by the use of a conventional pneumatic tourniquet cuff applied to the upper arm since there is less muscular tissue in the distal forearm.

With the distal forearm tourniquet 10 of the present invention, a majority of the surgery performed on the upper extremities involving the wrist, hand and fingers can now be performed under any type of regional anesthesia (i.e., blocks or local). Further, wrist blocks or local anesthesia combined with the distal forearm tourniquet 10 of the invention advantageously preserves active finger movement of the patient and is ideal for certain procedures such as the release of trigger fingers, tenolysis and possibly in connection with joint surgery. When the distal forearm tourniquet is applied, fingers flex automatically as if that person is actively bending the fingers. This gives the surgeon the opportunity to obtain the ideal length of tendon graft or transfer, especially when the muscles are paralyzed from anesthesia.

As mentioned above, the distal forearm tourniquet of the present invention is easily inflated with readily available manual sphygmomanometers 32 or compressed gas commonly found in operating suites. In addition, the chance of nerve damage from the distal forearm tourniquet of the invention is negligible since there are no nerves intimately located on any bone in the distal forearm.

It is also possible to use the distal forearm tourniquet 10 of the present invention as a backup in combination with a conventional pneumatic upper arm tourniquet cuff. Should the patient experience tourniquet pain in the upper arm, the distal forearm tourniquet can be applied and the upper arm tourniquet released, relieving the pain. Likewise, two tourniquets (upper arm and forearm) can be inflated alternately to reduce pain from either tourniquet. The tourniquet 10 of the invention is also very portable and simple to use and can be used in emergency rooms for minor surgery or to control bleeding, as well as by paramedics.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A method of controlling the flow of blood through a limb or part of a patient's body, comprising the steps of:
   (a) encircling and tightening a tourniquet about said limb or part to apply bidirectional pressure on both sides of a limb or part;
   (b) inflating an inflatable means located between the tourniquet strap and a desired portion of the limb or part so that the inflated inflatable means exerts a desired pressure directly against said desired portion and indirectly against the opposite side of aid desired portion, wherein said tourniquet is applied as a distal forearm tourniquet and wherein the tourniquet is applied with the inflatable means on the dorsal aspect and strap means on volar aspect of the forearm between the middle and distal $\frac{1}{3}$ to apply pressure to the posterior interosseous artery by the inflatable means and the anterior interosseous artery radial and ulnar arteries by the strap means.

2. The method of claim 1, wherein said tourniquet is applied as a distal forearm tourniquet during hand surgery.

3. The method of claim 1, wherein the inflatable means remains constantly inflated to said desired pressure by a pressurized air source during use.

4. The method of claim 3, wherein said pressurized air source is a manual sphygmomanometer.

* * * * *